US010013768B2

(12) United States Patent
Park et al.

(10) Patent No.: US 10,013,768 B2
(45) Date of Patent: Jul. 3, 2018

(54) METHOD AND APPARATUS FOR DISPLAYING IMAGE SHOWING OBJECT

(71) Applicant: SAMSUNG MEDISON CO., LTD., Hongcheon-gun (KR)

(72) Inventors: Sung-wook Park, Hongcheon-gun (KR); Jin-yong Lee, Hongcheon-gun (KR); Hyuk-jae Chang, Seoul (KR); Namsik Chung, Seoul (KR); Geu-ru Hong, Seoul (KR); Chi-young Shim, Seoul (KR); Ji-hyun Yoon, Seoul (KR); In-jeong Cho, Seoul (KR); Ran Heo, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 11 days.

(21) Appl. No.: 15/082,090

(22) Filed: Mar. 28, 2016

(65) Prior Publication Data
US 2017/0103534 A1   Apr. 13, 2017

(30) Foreign Application Priority Data
Oct. 7, 2015 (KR) .......................... 10-2015-0141044

(51) Int. Cl.
*G09G 5/24* (2006.01)
*G06T 7/00* (2017.01)
*G06T 11/00* (2006.01)

(52) U.S. Cl.
CPC .......... *G06T 7/0081* (2013.01); *G06T 7/0089* (2013.01); *G06T 11/00* (2013.01); *G06T 2207/10132* (2013.01); *G06T 2207/30004* (2013.01)

(58) Field of Classification Search
CPC .................................................... G06T 7/0081
USPC ........................................................... 345/642
See application file for complete search history.

(56) References Cited

U.S. PATENT DOCUMENTS

| | | | | | |
|---|---|---|---|---|---|
| 5,001,344 | A | * | 3/1991 | Kato | H01J 37/28 250/307 |
| 6,144,375 | A | * | 11/2000 | Jain | G06F 17/30017 345/420 |
| 6,314,197 | B1 | * | 11/2001 | Jain | G06K 9/00087 382/125 |
| 6,349,153 | B1 | * | 2/2002 | Teo | G06T 3/0081 358/450 |

(Continued)

FOREIGN PATENT DOCUMENTS

| EP | 2289418 A1 | 3/2011 |
|---|---|---|
| EP | 2883501 A2 | 6/2015 |

(Continued)

OTHER PUBLICATIONS

Communication dated Feb. 23, 2017 issued by the European Patent Office in counterpart European Patent Application No. 16154104.0.

*Primary Examiner* — Javid A Amini
(74) *Attorney, Agent, or Firm* — Sughrue Mion, PLLC

(57) ABSTRACT

Provided is a method and apparatus for displaying an image showing an object. The method of displaying an image showing an object includes: displaying a model corresponding to the object; receiving a user input for selecting, from the model, a region of interest (ROI) included in the object; and displaying an image showing the ROI based on the user input.

23 Claims, 16 Drawing Sheets

(56) References Cited

U.S. PATENT DOCUMENTS

| | | | |
|---|---|---|---|
| 7,796,155 B1* | 9/2010 | Neely, III | G06K 9/00771 |
| | | | 345/418 |
| 8,081,806 B2* | 12/2011 | Friedman | A61B 8/08 |
| | | | 382/128 |
| 8,094,772 B2* | 1/2012 | Grass | A61B 6/032 |
| | | | 378/4 |
| 8,214,011 B2* | 7/2012 | Friedman | A61B 8/00 |
| | | | 382/128 |
| 9,087,388 B2* | 7/2015 | Iwasaki | G06T 3/40 |
| 2003/0128205 A1* | 7/2003 | Varghese | G06T 17/00 |
| | | | 345/419 |
| 2005/0154305 A1 | 7/2005 | Kamiyama | |
| 2006/0233430 A1* | 10/2006 | Kimura | G06T 7/30 |
| | | | 382/128 |
| 2006/0290695 A1* | 12/2006 | Salomie | G06T 17/20 |
| | | | 345/420 |
| 2009/0130642 A1* | 5/2009 | Tada | A61B 8/14 |
| | | | 434/262 |
| 2009/0162820 A1* | 6/2009 | Tada | A61B 8/08 |
| | | | 434/272 |
| 2010/0007665 A1* | 1/2010 | Smith | G06T 13/40 |
| | | | 345/473 |
| 2012/0089016 A1* | 4/2012 | Mizuno | G06T 11/206 |
| | | | 600/425 |
| 2012/0128218 A1* | 5/2012 | Amyot | G06T 19/00 |
| | | | 382/128 |
| 2014/0136153 A1* | 5/2014 | Chen | G06T 19/20 |
| | | | 703/1 |
| 2014/0247284 A1* | 9/2014 | Gooding | G06T 7/174 |
| | | | 345/642 |
| 2016/0005211 A1* | 1/2016 | Sarkis | G06T 19/00 |
| | | | 345/419 |

FOREIGN PATENT DOCUMENTS

| | | |
|---|---|---|
| JP | 2007-68724 A | 3/2007 |
| JP | 201281037 A | 4/2012 |
| JP | 201290880 A | 5/2012 |
| WO | 2012099087 A1 | 7/2012 |

* cited by examiner

FIG. 6A
FIG. 6B
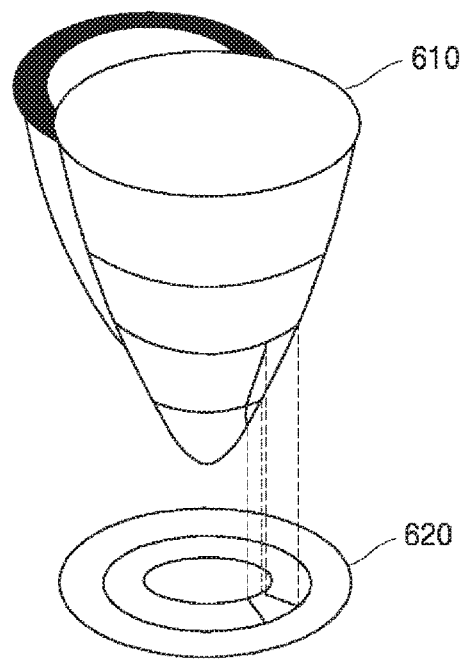
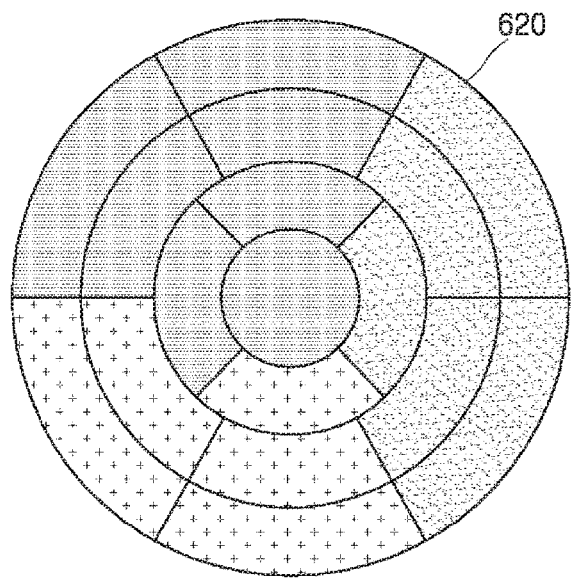

METHOD AND APPARATUS FOR DISPLAYING IMAGE SHOWING OBJECT

CROSS-REFERENCE TO RELATED APPLICATION

This application claims the benefit of Korean Patent Application No. 10-2015-0141044, filed on Oct. 7, 2015, in the Korean Intellectual Property Office, the disclosure of which is incorporated herein in its entirety by reference.

BACKGROUND

1. Field

The present disclosure relates to methods and apparatuses for displaying an image showing an object.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

However, users may often have difficulty in manipulating a three-dimensional (3D) image provided by an ultrasound diagnosis apparatus. In other words, when using an operation function provided by the ultrasound diagnosis apparatus to observe a 3D image at different angles or obtain a two-dimensional (2D) cross-sectional image, users frequently experience inconvenience related to the use of the operation function.

SUMMARY

Provided are methods and apparatuses for displaying an image showing an object.

Provided are non-transitory computer-readable recording media having recorded thereon programs for executing the methods of displaying an image showing an object on a computer.

Additional aspects will be set forth in part in the description which follows and, in part, will be apparent from the description, or may be learned by practice of the presented exemplary embodiments According to an aspect of an exemplary embodiment, a method of displaying an image showing an object includes: displaying a model corresponding to the object; receiving a user input for selecting, from the model, a region of interest (ROI) included in the object; and displaying an image showing the ROI based on the user input.

The receiving of the user input may include receiving a user input for selecting two different points in the model, and the displaying of the image showing the ROI may include displaying the image showing the ROI corresponding to a vector between the two different points.

The receiving of the user input may include receiving a user input for selecting two different points in the model, and the displaying of the image showing the ROI may include displaying the image showing the ROI corresponding to a normal vector. The normal vector may include a normal vector that is orthogonal to a vector between the two different points.

The method may further include receiving a user input for changing a position of at least one of the vector between the two different points and the normal vector, and the displaying of the image showing the ROI may include displaying the image showing the ROI corresponding to the at least one of the vector and the normal vector whose position has been changed.

The receiving of the user input may include receiving a user input for selecting one of a plurality of circles depicted on the model, and the displaying of the image showing the ROI may include displaying the image showing the ROI corresponding to the selected circle.

The receiving of the user input may include receiving a user input for selecting a point in the model, and the displaying of the image showing the ROI may include displaying the image showing the ROI corresponding to a vector between the selected point and a central point of the model.

The receiving of the user input may include receiving a user input for selecting one of a plurality of segments into which the model is partitioned, and the displaying of the image showing the ROI may include displaying the image showing the ROI corresponding to the selected segment.

The receiving of the user input may include receiving a user input for designating an angle corresponding to the ROI.

The method may further include receiving a user input for requesting enlargement or reduction of a shape of the ROI in the displayed image and displaying an image showing the ROI whose shape has been enlarged or reduced based on the user input.

The object may include an internal organ, and the model may include a two-dimensional (2D) image showing the internal organ.

The image showing the ROI may include a 2D image or a three-dimensional (3D) image.

According to an aspect of another exemplary embodiment, a non-transitory computer-readable recording medium includes a recording medium having recorded thereon a program for executing the above method on a computer.

According to an aspect of another exemplary embodiment, an apparatus for displaying an image showing an object includes: a display configured to display a model corresponding to the object; an input unit configured to receive a user input for selecting, from the model, an ROI included in the object; and an image processor configured to generate an image showing the ROI based on the user input, wherein the display displays the generated image.

The input unit may receive a user input for selecting two different points in the model, and the image processor may generate the image showing the ROI corresponding to a vector between the two different points.

The input unit may receive a user input for selecting two different points in the model, the image processor may generate the image showing the ROI corresponding to a normal vector, and the normal vector may include a normal vector that is orthogonal to a vector between the two different points.

The input unit may receive a user input for changing a position of at least one of the vector between the two different points and the normal vector, and the image processor may generate the image showing the ROI corresponding to the at least one of the vector and the normal vector whose position has been changed.

The input unit may receive a user input for selecting one of a plurality of circles depicted on the model, and the image processor may generate the image showing the ROI corresponding to the selected circle.

The input unit may receive a user input for selecting a point in the model, and the image processor may generate the image showing the ROI corresponding to a vector between the selected point and a central point of the model.

The input unit may receive a user input for selecting a point in the model, and the image processor may generate an image showing the ROI corresponding to a normal vector. The normal vector may include a normal vector that is orthogonal to a vector between the selected point and a central point of the model.

The input unit may receive a user input for selecting one of a plurality of segments into which the model is partitioned, and the image processor may generate the image showing the ROI corresponding to the selected segment.

The input unit may receive a user input for designating an angle corresponding to the ROI.

The input unit may receive a user input for requesting enlargement or reduction of a shape of the ROI in the displayed image, and the image processor may generate an image showing the ROI whose shape has been enlarged or reduced based on the user input.

The object may include an internal organ, and the model may include a 2D image showing the internal organ.

The image showing the ROI may include a 2D or 3D image.

BRIEF DESCRIPTION OF THE DRAWINGS

Embodiments of the invention now will be described more fully hereinafter with reference to the accompanying drawings, in which reference numerals denote structural elements:

FIGS. 6A and 6B are diagrams for explaining a model according to an exemplary embodiment;

DETAILED DESCRIPTION

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software. As used herein, the term "and/or" includes any and all combinations of one or more of the associated listed items. Expressions such as "at least one of," when preceding a list of elements, modify the entire list of elements and do not modify the individual elements of the list.

Throughout the specification, an "ultrasound image" refers to an image of an object, which is obtained using ultrasound waves or an image showing a region of interest (ROI) included in the object. An ROI refers to a region of an object that a user desires to observe with more focused attention, and, for example, may be a region including a lesion. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Hereinafter, exemplary embodiments will be described in detail with reference to the accompanying drawings.

Figure 1:
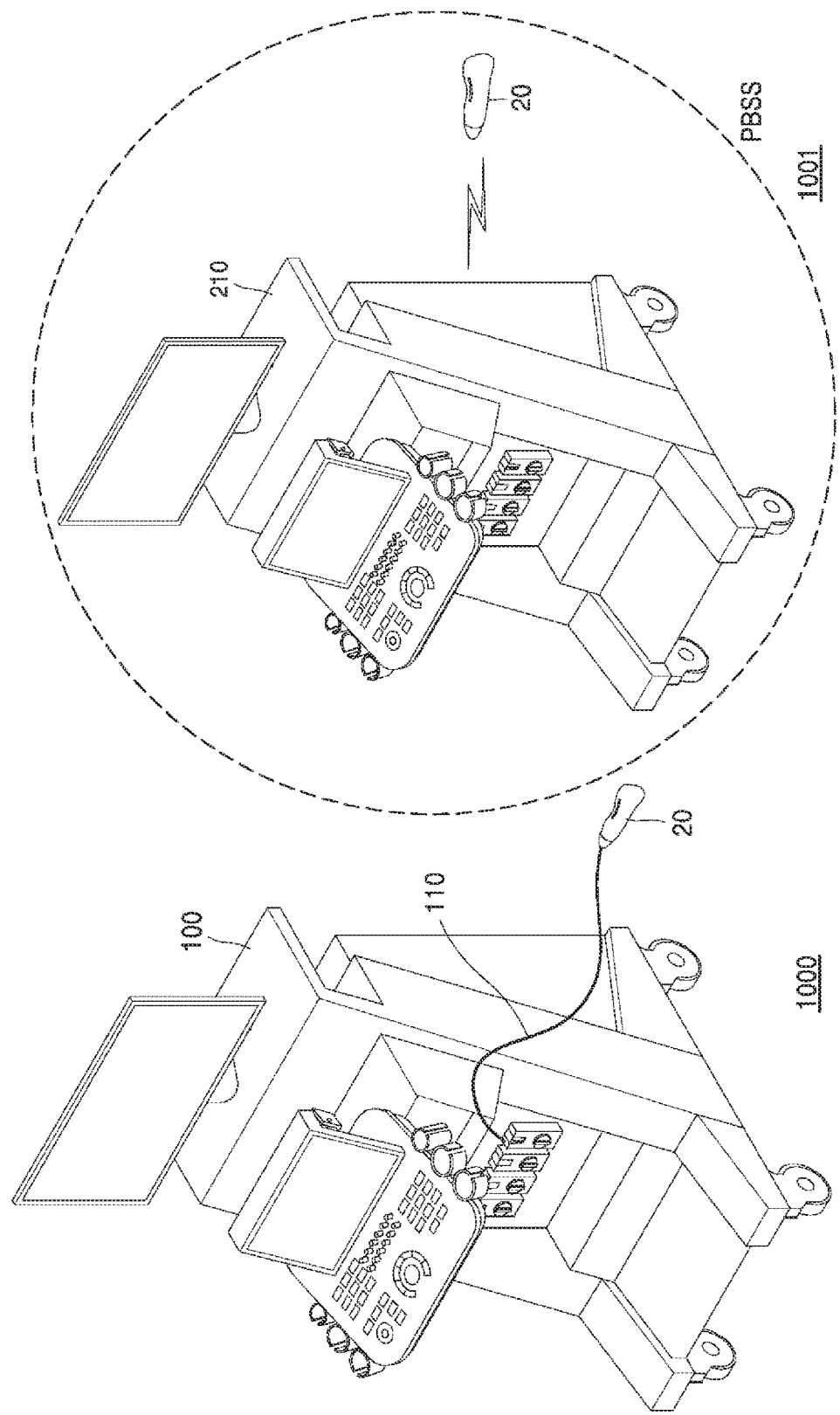
FIGS. 1A and 1B illustrate examples of ultrasound diagnosis systems according to exemplary embodiments.

FIGS. 1A and 1B are diagrams showing examples of ultrasound diagnosis systems 1000 and 1001 according to exemplary embodiments.

Referring to FIG. 1A, in the ultrasound diagnosis system 1000, a wired probe 20 may be connected by wire to an ultrasound imaging apparatus 100. In other words, the wired probe 20 for transmitting and receiving ultrasound waves may be connected to a main body of the ultrasound diagnosis system 1000, i.e., the ultrasound imaging apparatus 100 via a cable 110.

Referring to FIG. 1B, in the ultrasound diagnosis system 1001, a wireless probe 20 may be connected wirelessly to an ultrasound imaging apparatus 210. In other words, the probe 20 may be connected to the ultrasound imaging apparatus 210 via the same wireless network. For example, the probe 20 and the ultrasound imaging apparatus 210 may be combined with a Millimeter Wave (mmWave) based wireless network, and the probe 20 may transmit echo signals received through transducers to the ultrasound imaging apparatus 210 in the 60 GHz frequency band. The ultrasound imaging apparatus 210 may generate ultrasound images via various imaging modalities by using echo signals received in the 60 GHz frequency band and display the generated ultrasound images. In this case, the mmWave based wireless network may use a wireless communication method compliant with the WiGig standard developed by Wireless Gigabit Alliance (WGA), but is not limited thereto.

Figure 2:
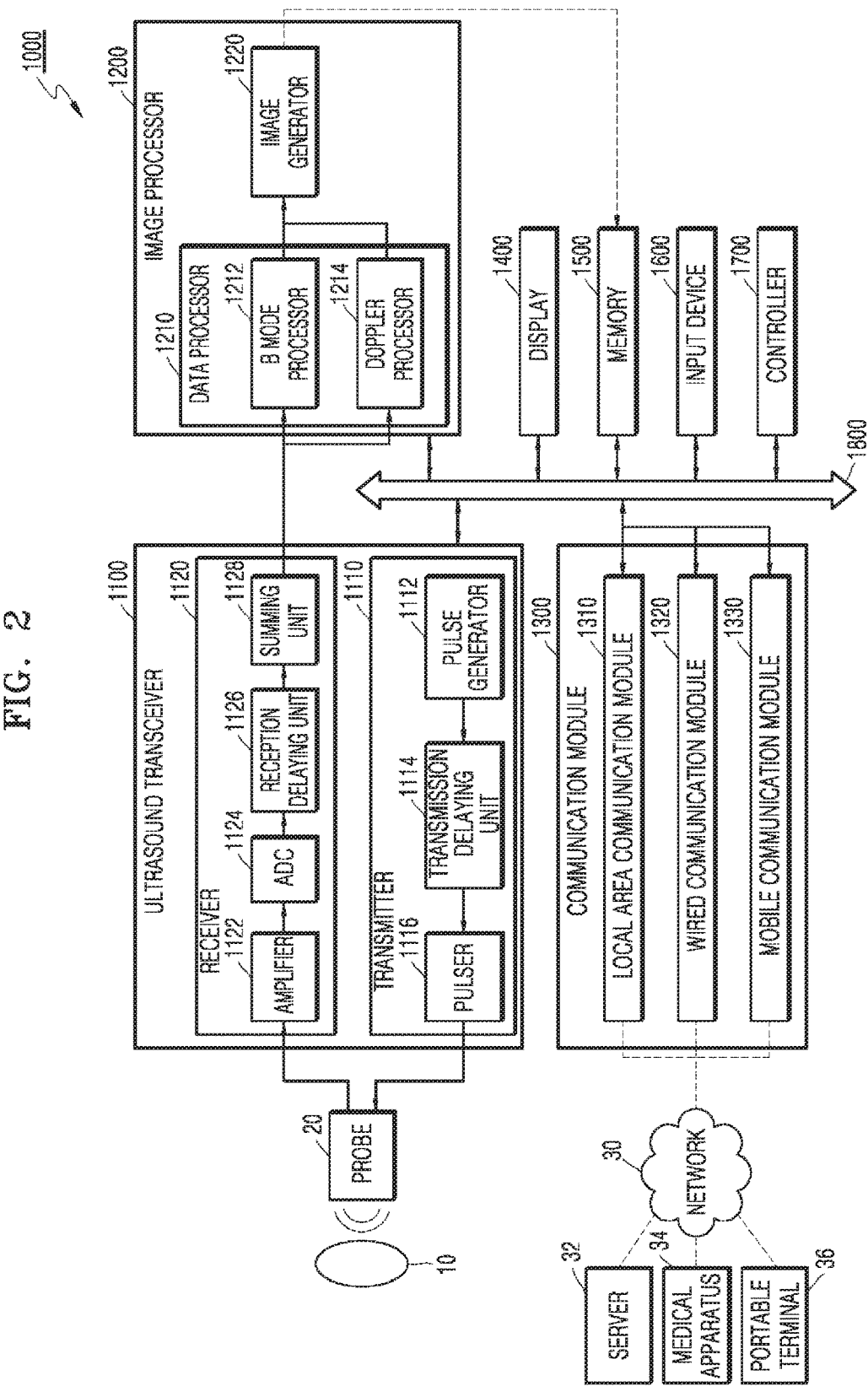
FIG. 2 is a diagram of a configuration of an ultrasound diagnosis system according to an exemplary embodiment.

FIG. 2 is a block diagram showing a configuration of an ultrasound diagnosis system 1002 according to an embodiment.

Referring to FIG. 2, the ultrasound diagnosis system 1002 may include a probe 20 and an ultrasound imaging apparatus 100. The ultrasound imaging apparatus 100 may include an ultrasound transceiver 1100, an image processor 1200, a communication module 1300, a display 1400, a memory 1500, an input unit 1600, and a controller 1700, which may be connected to one another via buses 1800.

For example, the ultrasound diagnosis system 1002 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 (or to an ROI in the object 10) in response to a driving signal applied by the ultrasound transceiver 1100 and receives echo signals reflected by the object 10 (or by the ROI in the object 10). The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis system 1002 by wire or wirelessly, and according to embodiments, the ultrasound diagnosis system 1002 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound imaging apparatus 1002 on a screen image via a graphical user interface (GUI). In addition, the ultrasound diagnosis apparatus 1002 may include two or more displays 1400 according to embodiments.

The communication module 1300 is connected to a network 30 by wire or wirelessly to communicate with an external device or a server. Furthermore, when the probe 20 is connected to the ultrasound imaging apparatus 1002 via a wireless network, the communication module 1300 may communicate with the probe 20.

The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of the object 10, such as ultrasound data and an ultrasound image that are input or output, and may also store algorithms or programs which are to be executed in the ultrasound diagnosis system 1002.

The memory 1500 may be any of various storage media, e.g., a flash memory, a hard disk drive, EEPROM, etc. Furthermore, the ultrasound diagnosis system 1002 may utilize web storage or a cloud server that performs the storage function of the memory 1500 online.

The input unit 1600 refers to a unit via which a user inputs data for controlling the ultrasound diagnosis system 1002. The input unit 1600 may include hardware components, such as a keyboard, a mouse, a touch pad, a touch screen, and a jog switch, and software modules for operating the hardware components. However, embodiments are not limited thereto, and the input unit 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

Furthermore, the input unit 1600 may receive a user input for selecting an ROI included in the object 10. In this case, the user input may include a user's touch gesture. Examples of a user's touch gesture may include tap, touch & hold, double tap, drag, panning, flick, drag & drop, pinch, stretch, etc.

For example, the user input may be a signal for selecting two different points in a model or a signal for changing a position of at least one of two different vectors represented in the model. Furthermore, the user input may be a signal for selecting one of a plurality of circles represented in the model or for drawing a circle on the model. Furthermore, the user input may be a signal for selecting a point in the model or for selecting one of a plurality of segments into which the model is partitioned. Furthermore, the user input may be a signal for enlarging or reducing a shape of an ROI included in the object 10 or for designating an angle corresponding to the ROI.

If the input unit 1600 is formed as a touch screen, the input unit 1600 may not only receive a user input but also perform the same function as the display 1400. In other words, the input unit 1600 may display and output an ultrasound image generated by the image processor 1200 and various pieces of information processed by the ultrasound imaging apparatus 1002 onto a screen via a graphical user interface (GUI). Furthermore, the input unit 1600 may display a model corresponding to the object 10 and an image showing an ROI generated by the image processor 1200 based on a user input.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input unit 1600 shown in FIG. 1.

All or some of the probe 20, the ultrasound transceiver 1100, the image processor 1200, the communication module 1300, the display 1400, the memory 1500, the input unit 1600, and the controller 1700 may be implemented as software modules. Also, at least one of the ultrasound transmission/reception unit 1100, the image processor 1200, and the communication module 1300 may be included in the controller 1700; however, the inventive concept is not limited thereto.

Figure 3:
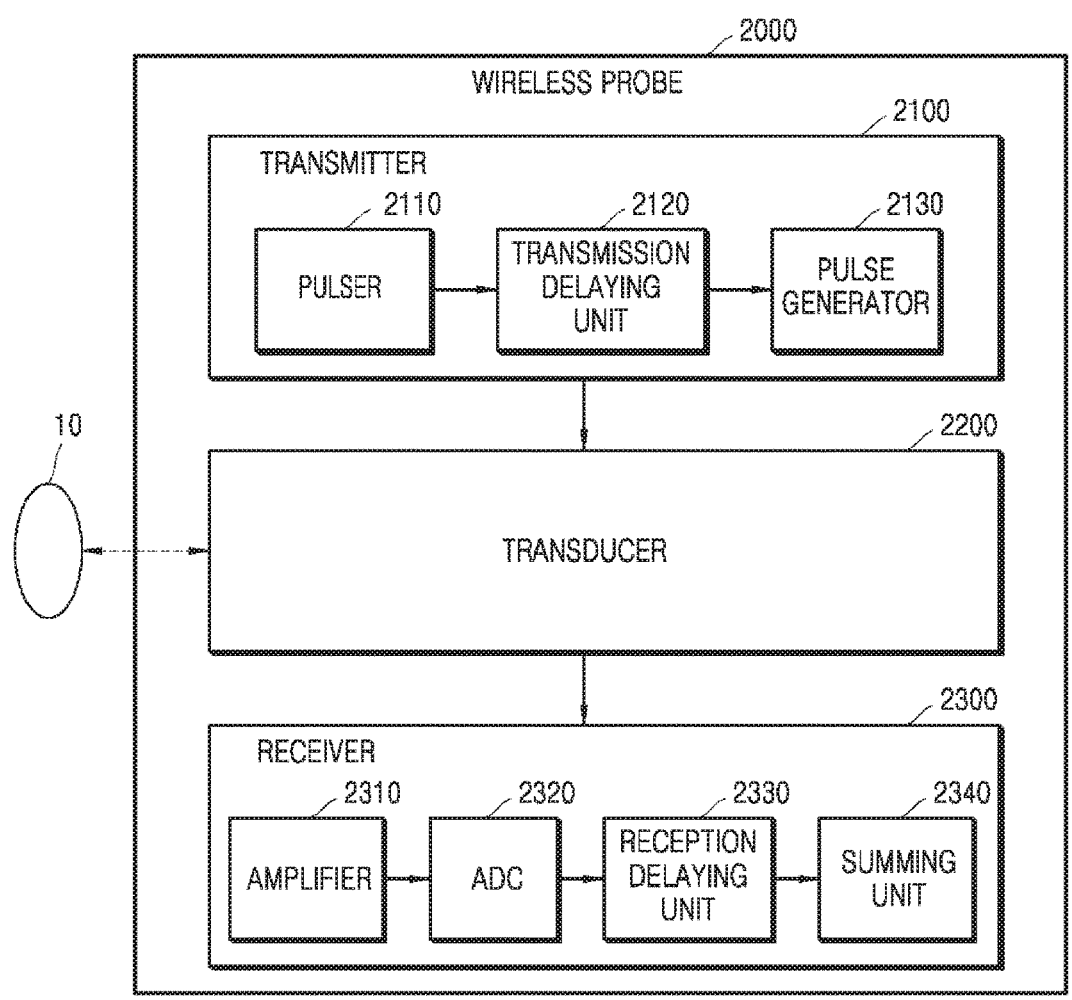
FIG. 3 is a diagram of a configuration of a wireless probe according to an exemplary embodiment.

FIG. 3 is a diagram showing a wireless probe 2000 according to an embodiment. As described above with reference to FIG. 2, the wireless probe 2000 may include a plurality of transducers, and, according to embodiments, may include some or all of the components of the ultrasound transceiver 1100 shown in FIG. 2.

The wireless probe 2000 according to the embodiment shown in FIG. 3 includes a transmitter 2100, a transducer 2200, and a receiver 2300. Since descriptions thereof are given above with reference to FIG. 2, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1002 shown in FIG. 2.

Figure 4A:
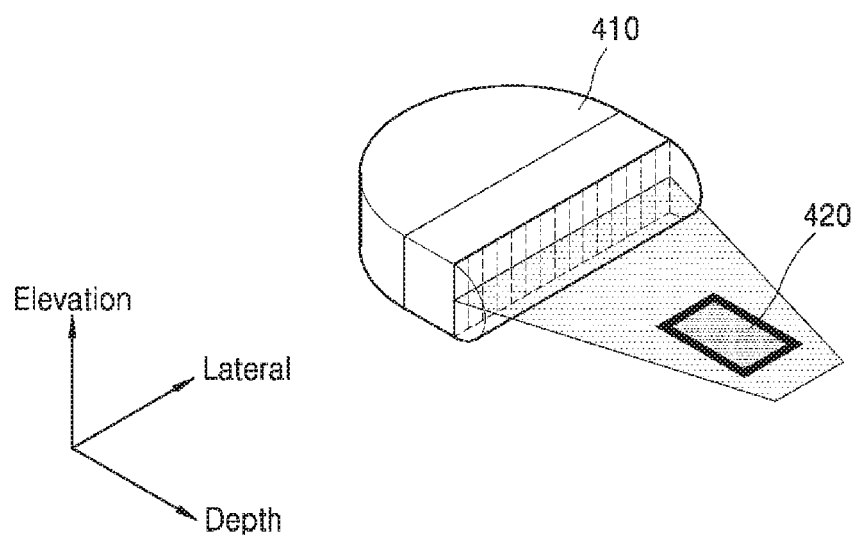
FIGS. 4A and 4B are diagrams illustrating examples in which a probe transmits ultrasound signals to an object, according to an exemplary embodiment.
Figure 4B:
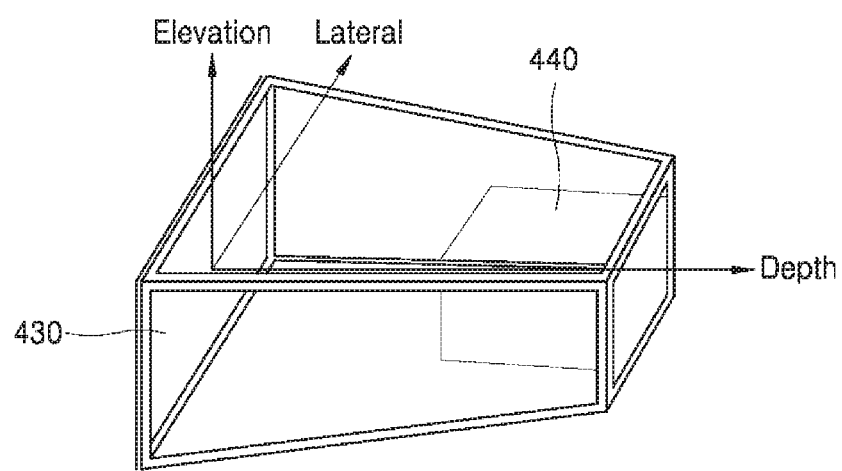

FIGS. 4A and 4B are diagrams illustrating examples in which a probe transmits ultrasound signals to an object, according to an exemplary embodiment.

Probes 410 and 430 respectively shown in FIGS. 4A and 4B may correspond to the wired probe 20 shown in FIG. 1A or the wireless probes 20 and 2000 respectively shown in FIGS. 1B and 3.

Referring to FIG. 4A, the probe 410 may be formed by a one-dimensional (1D) array of a plurality of transducers. In this case, the transducers are elements constituting the probe 410 and transmit ultrasound signals to an object 410 and receive echo signals reflected from the object 420. The plurality of transducers oscillate In response to reflected echo signals, generate electrical pulses corresponding to the oscillations, and output the electrical pulses to the ultrasound transceiver 1100.

Furthermore, transducers in the probe 410 may constitute an aperture or sub-array. In this case, the aperture is a set of some of the plurality of transducers in the probe 410. The number of transducers that constitute an aperture is not limited to a specific number, and one aperture may be composed of a single transducer.

Furthermore, referring to FIG. 4B, the probe 430 may be formed by a 2D array of a plurality of transducers. The probe 430 having the 2D array may transmit ultrasound signals to a 3D object 440 and receive echo signals reflected from the object 440. In this case, the probe 430 may transmit ultrasound signals to the object 440 and receive echo signals in the same manner as described with reference to FIG. 4A.

Figure 5:
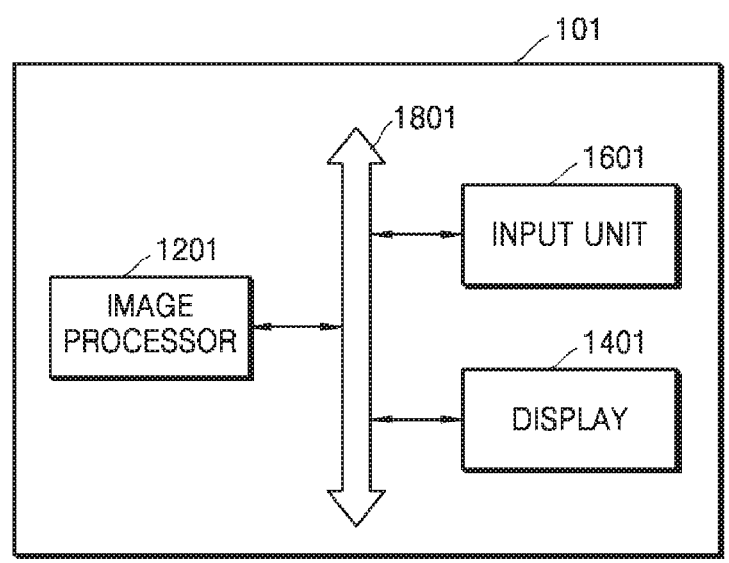
FIG. 5 is a diagram of a configuration of a display apparatus for displaying an image showing an object according to an exemplary embodiment.

FIG. 5 is a diagram of a configuration of a display apparatus 101 for displaying an image showing an object according to an exemplary embodiment.

Referring to FIG. 5, the display apparatus 101 includes an image processor 1201, a display 1401, and an input unit 1601, all of which are connected to one another via a bus 1801. In this case, all or some of the image processor 1201, the display 1401, and the input unit 1601 may be implemented using software modules, but are not limited thereto. Some of the components may also be implemented as hardware modules. Furthermore, the display apparatus 101 may include a controller (not shown) for controlling the image processor 1201, the display 1401, and the input unit 1601, and each of the image processor 1201, the display 1401, and the input unit 1601 may include an independent control module.

Furthermore, when the display apparatus 101 includes a touch screen, functions of the display 1401 and 1601 described below may be performed by the touch screen, as described above with reference to FIG. 2.

Furthermore, the image processor 1201, the display 1401, and the input unit 1601 may respectively correspond to the image processor 1200, the display 1400, and the input unit 1600 described with reference to FIG. 2. If the display apparatus 101 is included in the ultrasound imaging apparatus 1002, the display apparatus 101 may further include the ultrasound transceiver 1100, the communication module 1300, the memory 1500, and the controller 1700 described with reference to FIG. 2 in addition to the image processor 1201, the display 1401, and the input unit 1601.

The display 1401 displays a model corresponding to the object 10. For example, the image processor 1201 may generate a model corresponding to the object 10, and the display 1401 may display the generated model on a screen. For example, the image processor 1201 may generate a model corresponding to the object 10 currently being scanned and transmit the generated model to the display 1401. As another example, the image processor 1201 may generate models for respective ones of a plurality of applications in advance, store the generated models in a memory (not shown), and read out a model for an application corresponding to the object 10 from the memory. In this case, an application refers to a diagnostic field, and the type of application may be determined based on a part or internal organ of a human or animal body.

The model refers to an image showing an outlined shape of the object 10. In this case, the object 10 may be an internal organ, and the model may be a 2D image showing the internal organ. For example, if the object 10 is the heart, the model refers to a 2D or 3D image showing an outlined shape of the heart. The model will now be described with reference to FIGS. 6A and 6B.

FIGS. 6A and 6B are diagrams for explaining a model according to an exemplary embodiment.

FIG. 6A shows an example of a model 620 corresponding to an object 610. For example, if the object 610 is the heart, the model 620 may be formed by projecting a 3D shape of the heart onto a plane.

FIG. 6B shows an example of the model 620. Referring to FIG. 6B, the model 620 may be partitioned into a plurality of segments, each of which may be a portion of the partitioned object 610 based on an anatomical theory. Thus, the model 620 may be represented by a combination of all portions of the object 10.

Referring back to FIG. 5, the input unit 1601 receives a user input for selecting, from a model, an ROI of the object 10. The ROI refers to a region of the object 10 that a user desires to observe with more focused attention. For example, the ROI may be a region corresponding to one cross-section of the object 10 or a portion of a surface of the object 10.

For example, the user input may be a signal for selecting two different points in a model and a signal for changing a position of at least one of two different vectors represented in the model. Furthermore, the user input may be a signal for selecting one of a plurality of circles represented in the model or for drawing a circle on the model. Furthermore, the user input may be a signal for selecting a point in the model or for selecting one of a plurality of segments into which the model is partitioned. Furthermore, the user input may be a signal for enlarging or reducing a shape of an ROI included in the object 10 or for designating an angle corresponding to the ROI.

The display 1401 displays an image showing an ROI based on a user input. In detail, the image processor 1201 generates an image showing an ROI based on the user input, and the display 1401 displays an image generated by the image processor 1201 on a screen.

The image processor 1201 may identify an ROI selected based on a user input and generate an image showing an ROI by using previously generated image data (e.g., ultrasound data). In detail, the image processor 1201 generates an image showing a cross-section of the object 10. For example, the image processor 1201 may generate a 2D image and/or a 3D image showing a cross-section of the object.

The display 1401 displays an image showing an ROI generated by the image processor 1201. First, the display 1401 displays an initial screen and a model showing the object 10 on a screen. Then, when the input unit 1601 receives a user input for selecting an ROI, the image processor 1201 generates an image showing the ROI. Subsequently, the display 1401 may display the image showing the ROI on the screen, together with the model. In this case, the initial screen that was initially output to the screen may not be displayed and be replaced with the image showing the ROI, or the image showing the ROI and the initial screen may be displayed together on the screen.

Examples in which the display apparatus 101 outputs an initial screen will now be described with reference to FIG. 7. It is assumed in FIGS. 7 through 15 that the object 10 is the heart, and the object 10 is not limited to the heart as described above.

Figure 7:
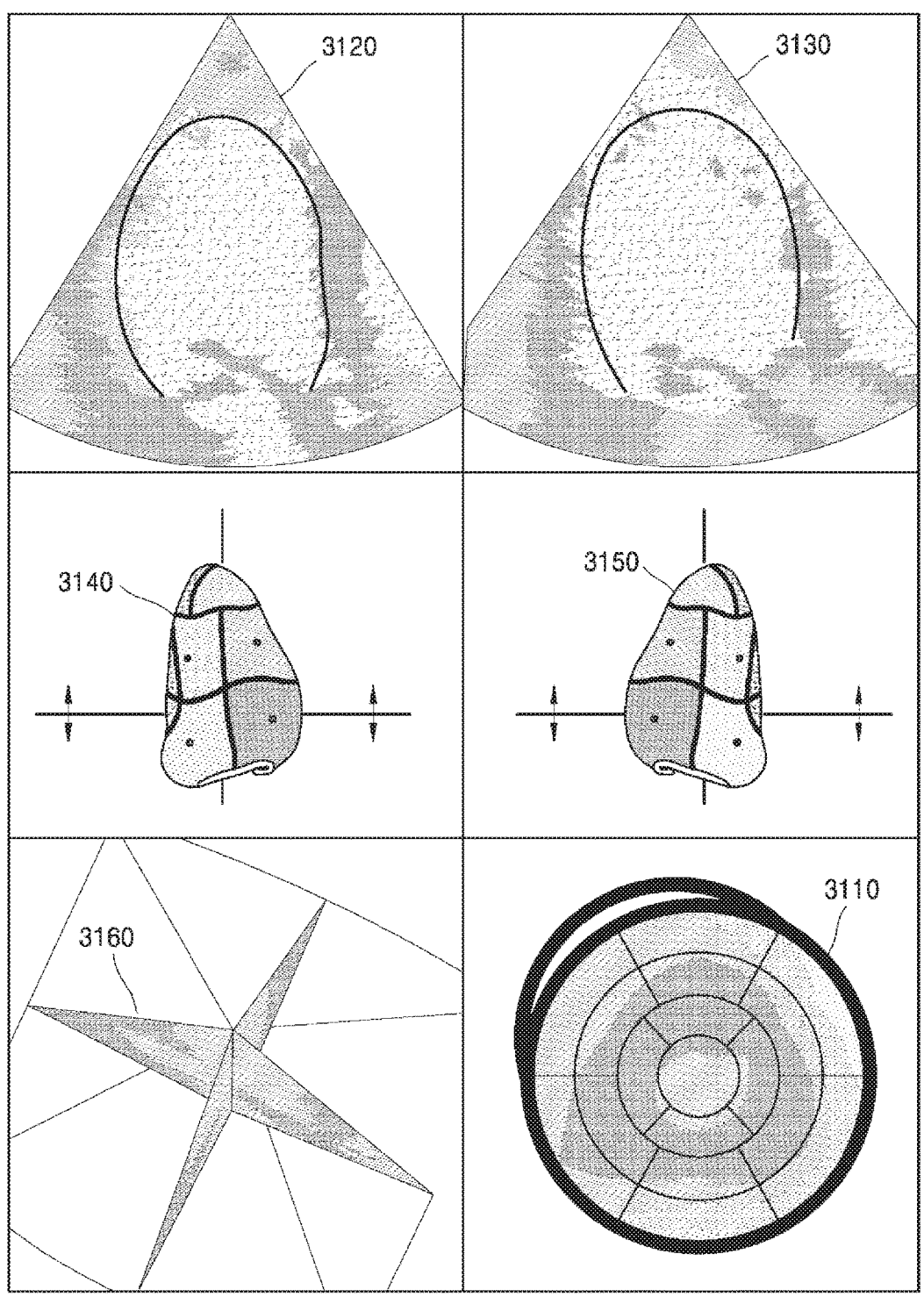
FIG. 7 is a diagram illustrating an example of an initial screen output onto a display apparatus according to an exemplary embodiment.

FIG. 7 is a diagram illustrating an example of an initial screen output onto the display apparatus 101 according to an exemplary embodiment.

FIG. 7 shows an example of an initial screen 3100 output onto the display 1401. For example, the initial screen 3100 may include not only a model 3110 but also various images 3120, 3130, 3140, 3150, and 3160 showing the heart. For example, the initial screen 3100 may include 2D images 3120 and 3130 showing cross-sections of the heart, 3D images 3140 and 3150 corresponding to the cross-sections, and an image 3160 showing a position relationship between the cross-sections. However, the number and type of images included in the initial screen 3100 are not limited to the example illustrated in FIG. 7.

Views of the images 3120, 3130, 3140, and 3150 included in the initial screen 3100 may be preset. For example, a view may be set during the manufacture of the display apparatus 101, or a user of the display apparatus 101 may change the preset view.

When the user selects an ROI in the model 3110, the image processor 1201 generates a 2D or 3D image showing the ROI. The display 1401 may replace the images 3120, 3130, 3140, 3150, and 3160 included in the initial screen 3100 with images showing the ROI. Alternatively, the display 1401 may display the images 3120, 3130, 3140, 3150, and 3160 together with images showing the ROI. Furthermore, the display 1401 may display the model 3110 having indicated thereon a line, a dot, or a circle corresponding to a user input.

The user may select an ROI by perform a gesture on the model 3110 or using an input device such as a keyboard, a mouse, a touch pad, a trackball, a jog switch, or the like. For example, if the screen of the display apparatus 1401 is a touch screen, functions of the input unit 1601 and the display 1401 may be performed via the touch screen as described above with reference to FIGS. 2 and 5. Thus, if the screen of the display apparatus 101 is a touch screen, the user may select an ROI by performing a gesture on the model 3110 output on the screen.

Examples in which a model and images showing an ROI are displayed will be described in detail below with reference to FIGS. 8 through 15.

Figure 8:
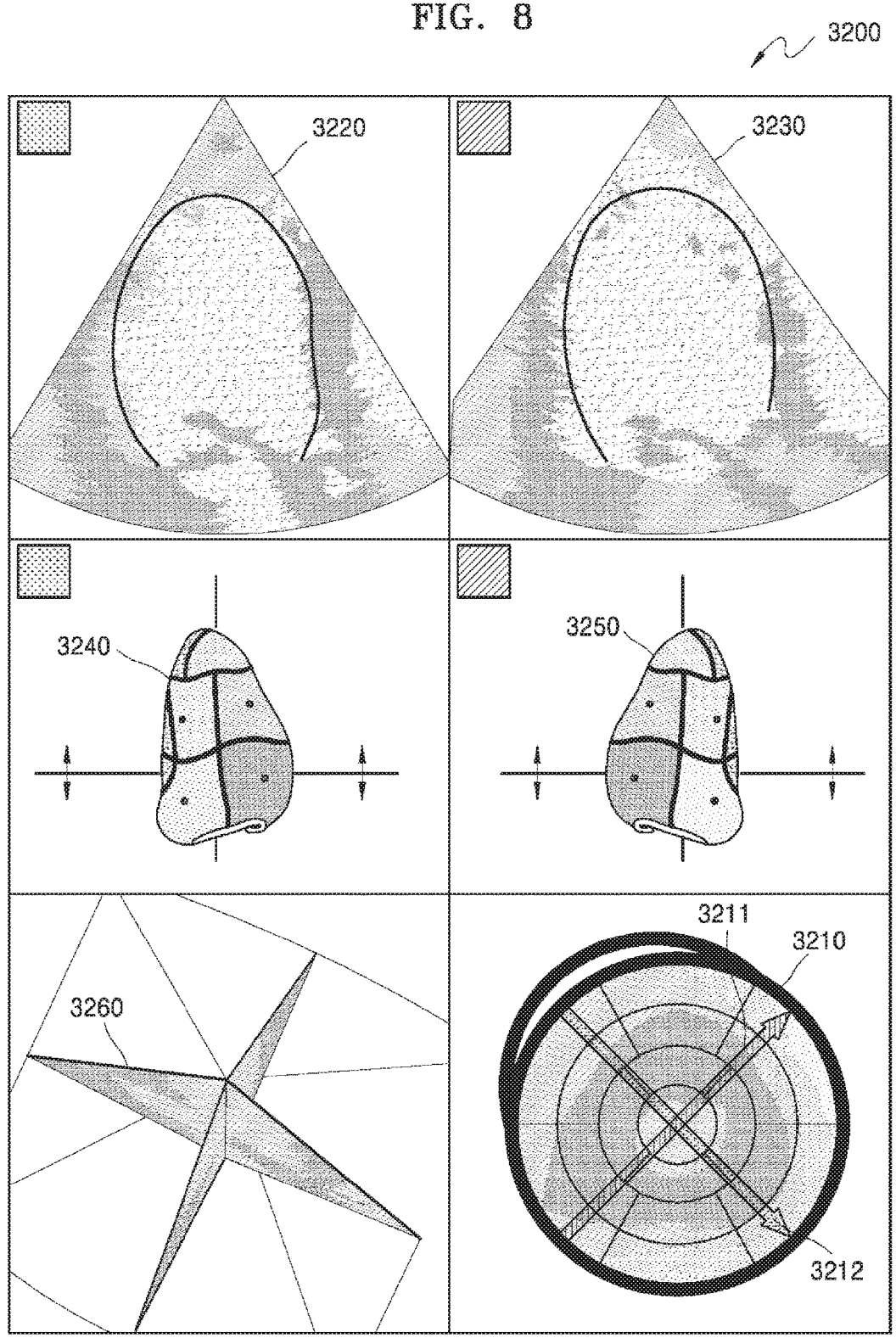
FIG. 8 is a diagram for explaining an example of an operation of a display apparatus according to an exemplary embodiment.

FIG. 8 is a diagram for explaining an example of an operation of the display apparatus 101 according to an exemplary embodiment.

FIG. 8 illustrates an example of a screen 3200 on which a model 3210 and images 3220, 3230, 3240, 3250, and 3260 are output.

As described above with reference to FIG. 7, the user may select an ROI in the model 3110 output on the initial screen 3100. In this case, the user input may be an input for selecting two different points in the model 3110. For example, the user may select the two different points by performing a gesture on the model 3110 or by using an input device.

When the user input for selecting the two different points are received, the display 1401 displays a vector 3211 between the selected two different points on the model 3210. In other words, the display 1401 displays on the model 3210 the vector 3211 that starts at a point initially selected by the user and ends at a point lastly selected by the user.

The image processor 1201 identifies a cross-section corresponding to the vector 3211 as an ROI and generates a 2D image 3220 and a 3D image 3230, which both show the ROI. The display 1401 then displays the 2D image 3220 and the 3D image 3230 on the screen 3200.

Furthermore, the display 1401 may display a normal vector 3212 that is orthogonal to the vector 3211 on the model 3210. The image processor 1201 uses a cross-section corresponding to the normal vector 3212 as an ROI and generates a 2D image 3240 and a 3D image 3250, which both show the ROI. The display 1401 may display the 2D image 3240 and the 3D image 3250 on the screen 3200.

Furthermore, the display 1401 may display an image 3260 showing a position relationship between the 2D images 3220 and 3240 on the screen 3200.

Figure 9:
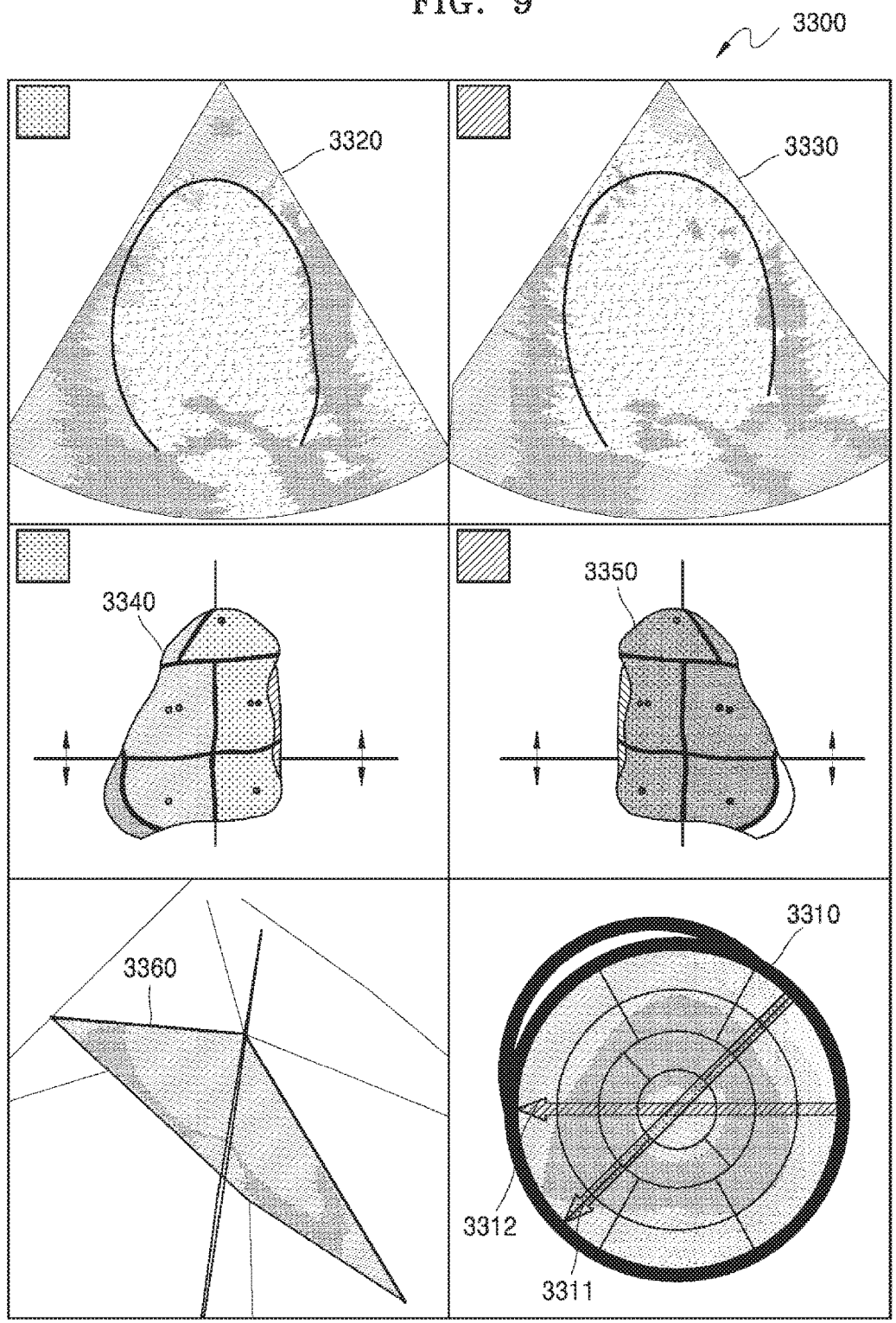
FIG. 9 is a diagram for explaining another example of an operation of a display apparatus according to an exemplary embodiment.

FIG. 9 is a diagram for explaining another example of an operation of the display apparatus 101 according to an exemplary embodiment.

FIG. 9 illustrates an example of a screen 3300 on which a model 3310 and images 3320, 3330, 3340, 3350, and 3360 are output.

As described above with reference to FIG. 8, the user may select two points that constitute the vector 3211. The image processor 1201 generates the 2D and 3D images 3220 and 3230 corresponding to the vector 3211 and the 2D and 3D images corresponding to the normal vector 3212 that is orthogonal to the vector 3211. The display 1401 displays the generated 2D and 3D images 3220, 3230, 3240, and 3250 on the screen 3200.

Subsequently, the user may change a position (s) of the vector 3211 and/or the normal vector 3212. For example, the user may change the position (s) of the vector 3211 and/or the normal vector 3212 by performing a gesture on the model 3210 or by using an input device.

When a user input for changing the position (s) of the vector 3211 and/or the normal vector 3212 is received, the display 1401 displays a vector 3311 and/or a normal vector 3312 whose position (s) has (have) been changed on the model 3310.

The image processor 1201 identifies a cross-section corresponding to the vector 3311 as an ROI and generates a 2D image 3320 and a 3D image 3330, which both show the ROI. The display 1401 then displays the 2D image 3320 and the 3D image 3330 on the screen 3300.

Furthermore, the image processor 1201 identifies a cross-section corresponding to the normal vector 3312 as an ROI and generates a 2D image 3340 and a 3D image 3350, which both show the ROI. The display 1401 displays the 2D image 3340 and the 3D image 3350 on the screen 3300.

In addition, the display 1401 may display an image 3360 showing a position relationship between the 2D images 3320 and 3340 on the screen 3300.

Figure 10:
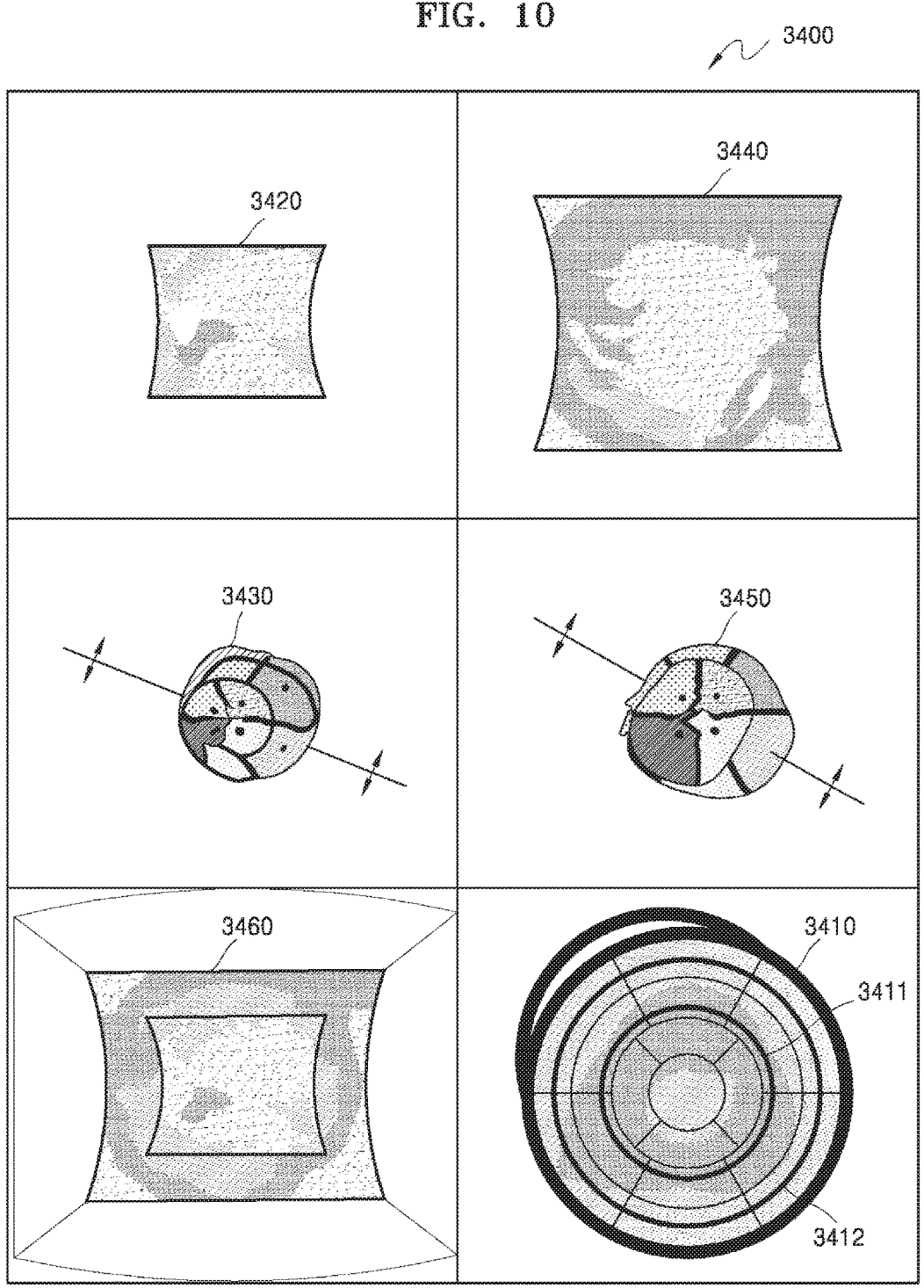
FIG. 10 is a diagram for explaining another example of an operation of a display apparatus according to an exemplary embodiment.

FIG. 10 is a diagram for explaining another example of an operation of the display apparatus 101 according to an exemplary embodiment.

FIG. 10 illustrates an example of a screen 3400 on which a model 3410 and images 3420, 3430, 3440, 3450, and 3460 are output.

As described above with reference to FIG. 7, the user may select an ROI in the model 3110 output on the initial screen 3100. For example, a user input may be an input for selecting at least one circle from among a plurality of circles 3411 and 3412 depicted on the model 3410. As another example, the user input may be an input for drawing at least one circle 3411 or 3412 on the model 3410. For example, the user may select at least one circle from among the plurality of circles 3411 and 3412 or draw at least one circle 3411 or 3412 by performing a gesture on the model 3410 or by using an input device.

When a user input for drawing at least one circle 3411 or 3412 on the model 3410 is received, the display 1401 displays the at least one circle 3411 or 3412 on the model 3410.

The image processor 1201 identifies a cross-section corresponding to the circle 3411 as an ROI to generate a 2D image 3420 and a 3D image 3430, which both show the ROI. The display 1401 then displays the 2D image 3420 and the 3D image 3430 on the screen 3400.

Furthermore, the image processor 1201 identifies a cross-section corresponding to the circle 3412 as an ROI to generate a 2D image 3440 and a 3D image 3450, which both show the ROI. The display 1401 may then display the 2D image 3440 and the 3D image 3450 on the screen 3400.

In addition, the display 1401 may display an image 3460 showing a position relationship between the 2D images 3420 and 3440 on the screen 3400.

Figure 11:
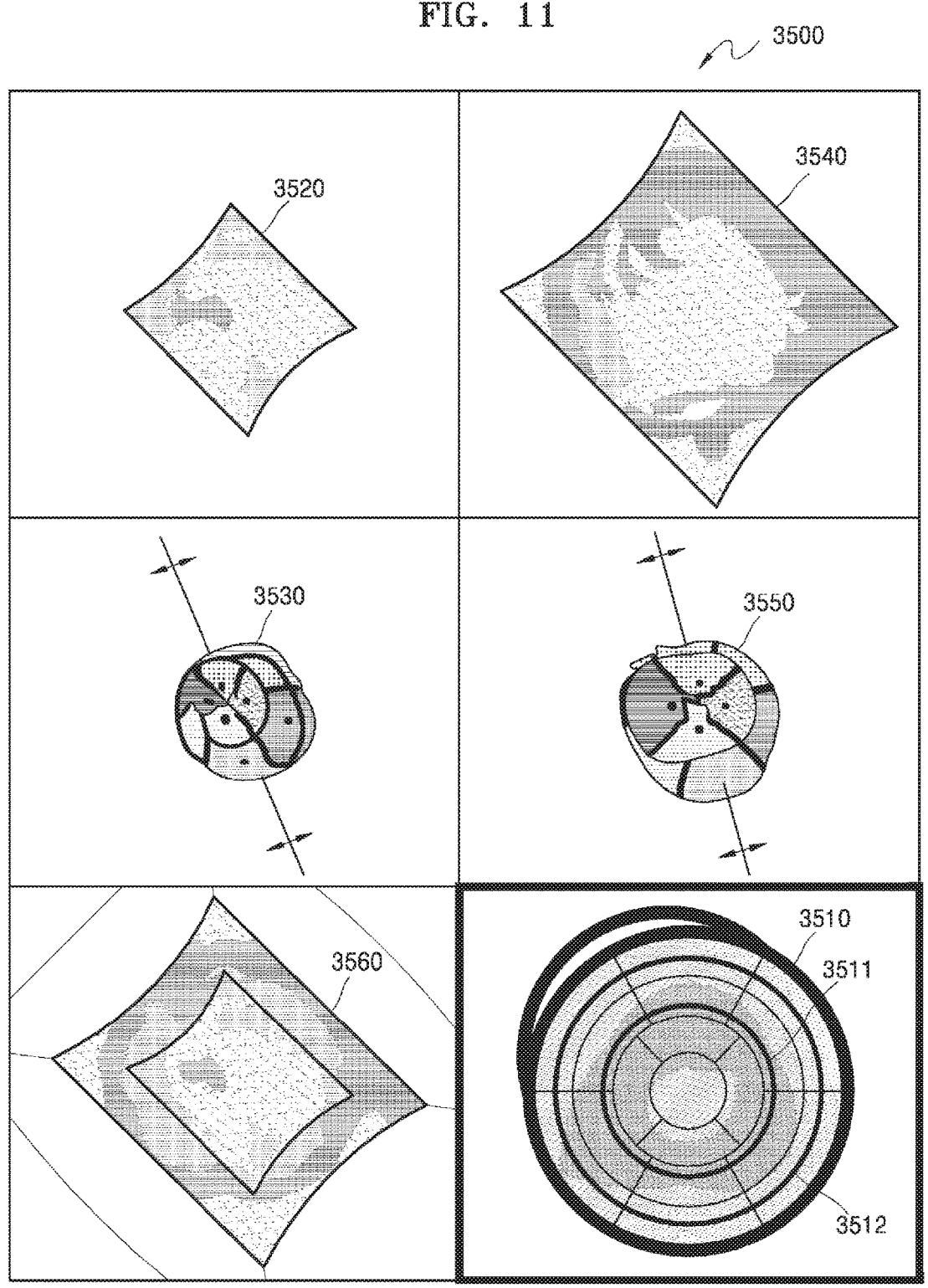
FIG. 11 is a diagram for explaining another example of an operation of a display apparatus according to an exemplary embodiment.

FIG. 11 is a diagram for explaining another example of an operation of the display apparatus 101 according to an exemplary embodiment.

FIG. 11 illustrates an example of a screen 3500 on which a model 3510 and images 3520, 3530, 3540, 3550, and 3560 are output.

As described above with reference to FIG. 10, the user may select at least one circle from among the plurality of circles 3411 and 3412 depicted on the model 3410 or draw the at least one circle 3411 or 3412 on the model 3410 The image processor 1201 generates the 2D and 3D images 3420 and 3430 corresponding to the circle 3411 and the 2D and 3D images 3440 and 3450 corresponding to the circle 3412. The display 1401 displays the 2D and 3D images 3420, 3430, 3440, and 3450 on the screen 3400.

Subsequently, the user may rotate the circle(s) 3411 and/or 3412. For example, the user may rotate the circle(s) 3411 and/or 3412 by performing a gesture on the model 3410 or by using an input device.

When a user input for rotating the circle(s) 3411 and/or 3412 is received, the display 1401 displays the rotated circle(s) 3511 and/or 3512 on the model 3510.

The image processor 1201 identifies a cross-section corresponding to the rotated circle 3511 as an ROI to generate a 2D image 3520 and a 3D image 3530. The display 1401 then displays the generated 2D and 3D images 3520 and 3530 on the screen 3500.

Furthermore, the image processor 1201 identifies a cross-section corresponding to the rotated circle 3512 as an ROI to generate a 2D image 3540 and a 3D image 3550. The display 1401 then displays the generated 2D and 3D images 3540 and 3550 on the screen 3500.

In addition, the display 1401 may display an image 3560 showing a position relationship between the 2D images 3520 and 3540 on the screen 3500.

Figure 12B:
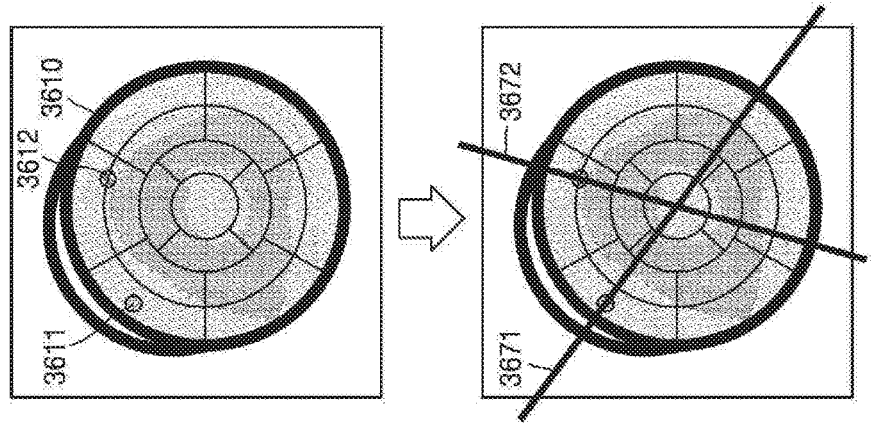
FIGS. 12A and 12B are diagrams for explaining another example of an operation of a display apparatus according to an exemplary embodiment.
Figure 12A:
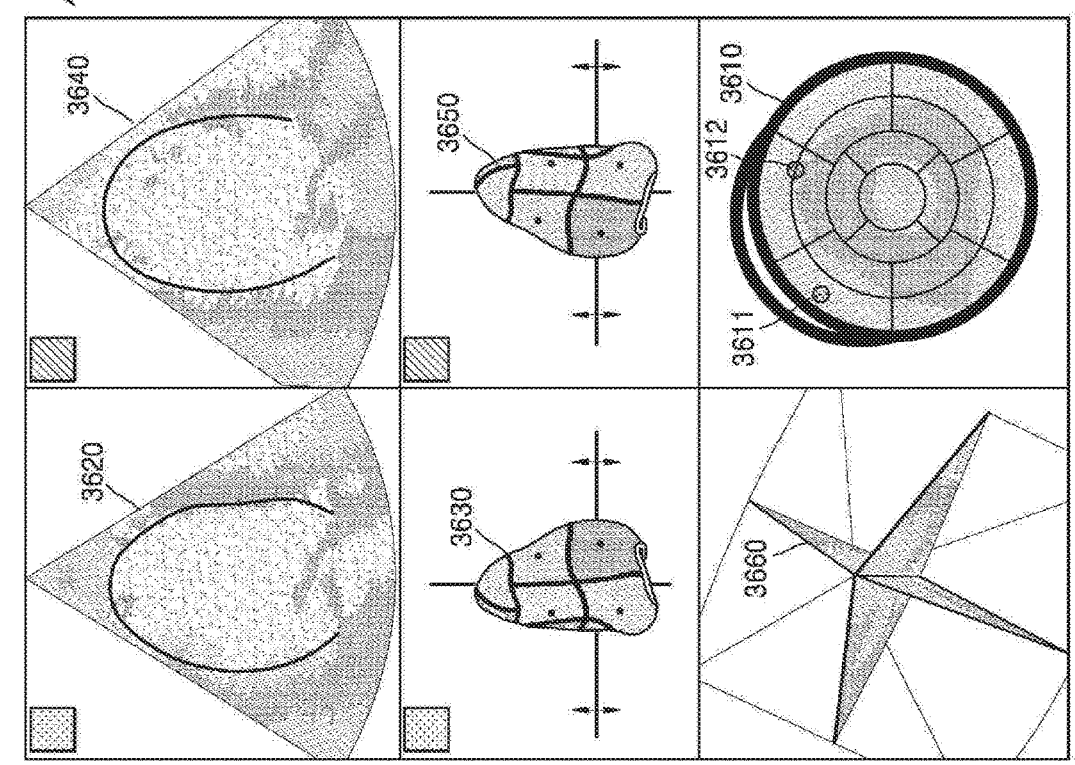

FIGS. 12A and 12B are diagrams for explaining another example of an operation of the display apparatus 101 according to an exemplary embodiment.

FIG. 12A illustrates an example of a screen 3600 on which a model 3610 and images 3620, 3630, 3640, 3650, and 3660 are output.

As described above with reference to FIG. 7, the user may select an ROI in the model 3110 output on the initial screen 3100. In this case, a user input may be an input for selecting one point in the model 3110. For example, the user may select one point by performing a gesture on the model 3110 or by using an input device.

When a user input for selecting one point 3611 is received, the display 1401 displays the selected point 3611 on the model 3610. The image processor 1201 uses a cross-section corresponding to a straight line including the point 3611 as an ROI to generate a 2D image 3620 and a 3D image 3630, which both show the ROI. The display 1401 then displays the 2D image 3620 and the 3D image 3630 on the screen 3600.

Furthermore, the user may select another point 3612 as well as the point 3611 in the model 3610. When a user input for selecting the point 3612 is received, the display 1401 displays the selected point 3612 on the model 3610. The image processor 1201 uses a cross-section corresponding to a straight line including the point 3612 as an ROI to generate a 2D image 3640 and a 3D image 3650, which both show the ROI. The display 1401 then displays the 2D image 3640 and the 3D image 3650 on the screen 3600.

Furthermore, the display 1401 may display an image 3660 showing a position relationship between the 2D images 3620 and 3640 on the screen 3600.\

Referring to FIG. 12B, the two points 3611 and 3620 selected by the user are indicated on the model 3610. To generate the 2D image 3620 and the 3D image 3630, the image processor 1201 computes a vector 3671 that starts at the point 3611 and ends at a central point of the model 3610. Then, the image processor 1201 uses a cross-section corresponding to the vector 3671 as an ROI to generate the 2D image 3620 and the 3D image 3630, which both show the ROI.

Furthermore, to generate the 2D image 3640 and the 3D image 3650, the image processor 1201 computes a vector 3672 that starts at the point 3612 and ends at the central point of the model 3610. Then, the image processor 1201 uses a cross-section corresponding to the vector 3672 as an ROI to generate the 2D image 3640 and the 3D image 3650, which both show the ROI.

Figure 13:
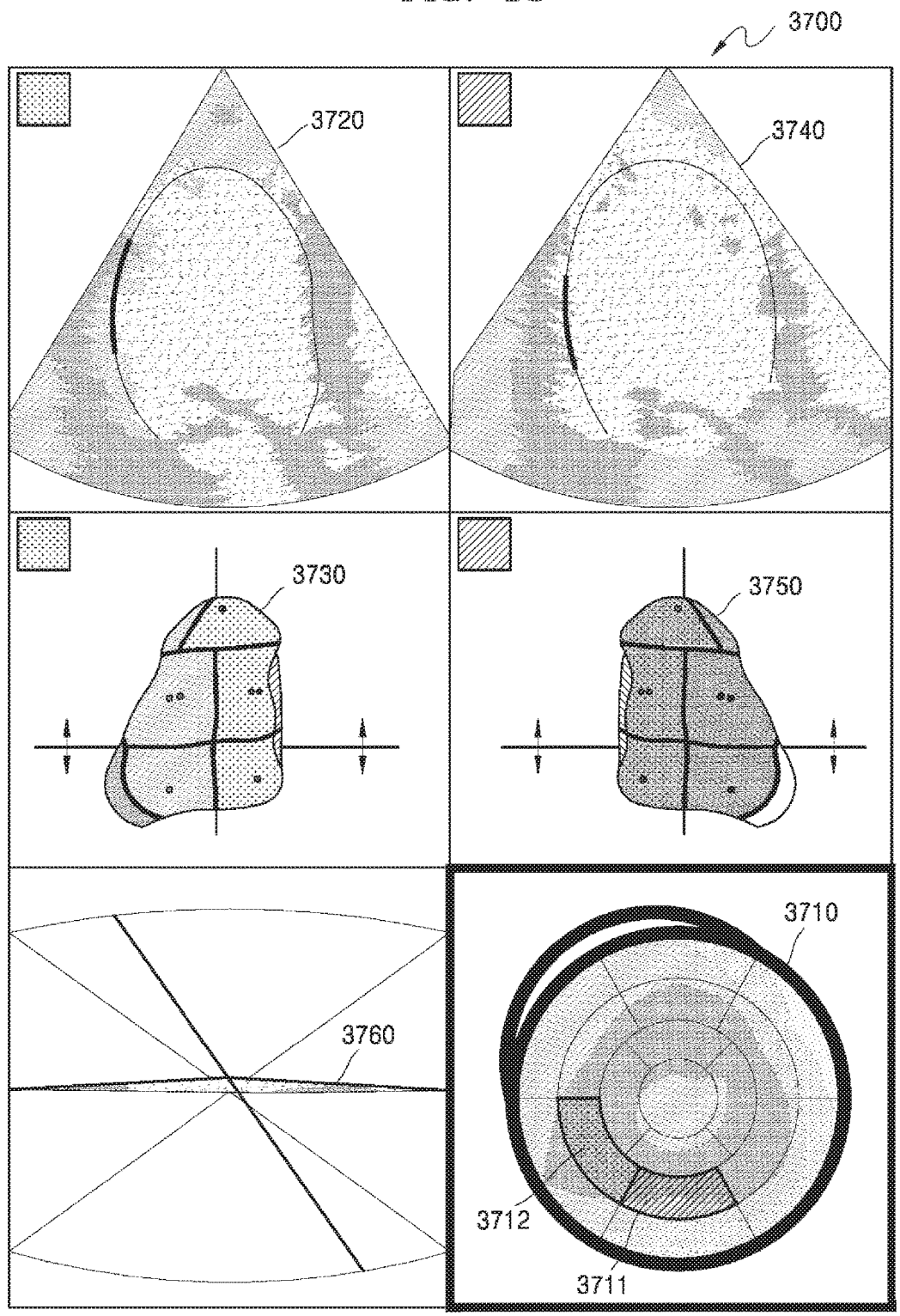
FIG. 13 is a diagram for explaining another example of an operation of a display apparatus according to an exemplary embodiment.

FIG. 13 is a diagram for explaining another example of an operation of the display apparatus 101 according to an exemplary embodiment.

FIG. 13 illustrates an example of a screen 3700 on which a model 3710 and images 3720, 3730, 3740, 3750, and 3760 are output.

As described above with reference to FIG. 7, the user may select an ROI in the model 3110 output on the initial screen 3100. In this case, a user input may be an input for selecting one of a plurality of segments into which the model 3710 is partitioned. For example, the user may select a segment by performing a gesture on the model 3710 or by using an input device.

When a user input for selecting a segment 3711 is received, the display 1401 displays the selected segment 3711 on the model 3710 in such a manner as to be distinguished from non-selected segments. For example, the display 1401 may display the selected segment 3711 in a different color than the non-selected segments.

The image processor 1201 identifies a cross-section corresponding to the segment 3711 as an ROI to generate a 2D image 3720 and a 3D image 3730, which both show the ROI. The display 1401 then displays the 2D image 3720 and the 3D image 3730 on the screen 3700.

Furthermore, the user may select another segment 3712 as well as the previously selected segment 3711 from among the plurality of segments into which the model 3710 is partitioned. When a user input for selecting the other segment 3712 is received, the display 1401 displays the selected segment 3712 on the model 3710 in such a manner as to be distinguished from non-selected segments. The image processor 1201 then uses a cross-section corresponding to the segment 3712 as an ROI to generate a 2D image 3740 and a 3D image 3750, which both show the ROI. The display 1401 then displays the 2D image 3740 and the 3D image 3750 on the screen 3700.

In addition, the display 1401 may display an image 3760 showing a position relationship between the 2D images 3720 and 3740 on the screen 3700.

Figure 14:
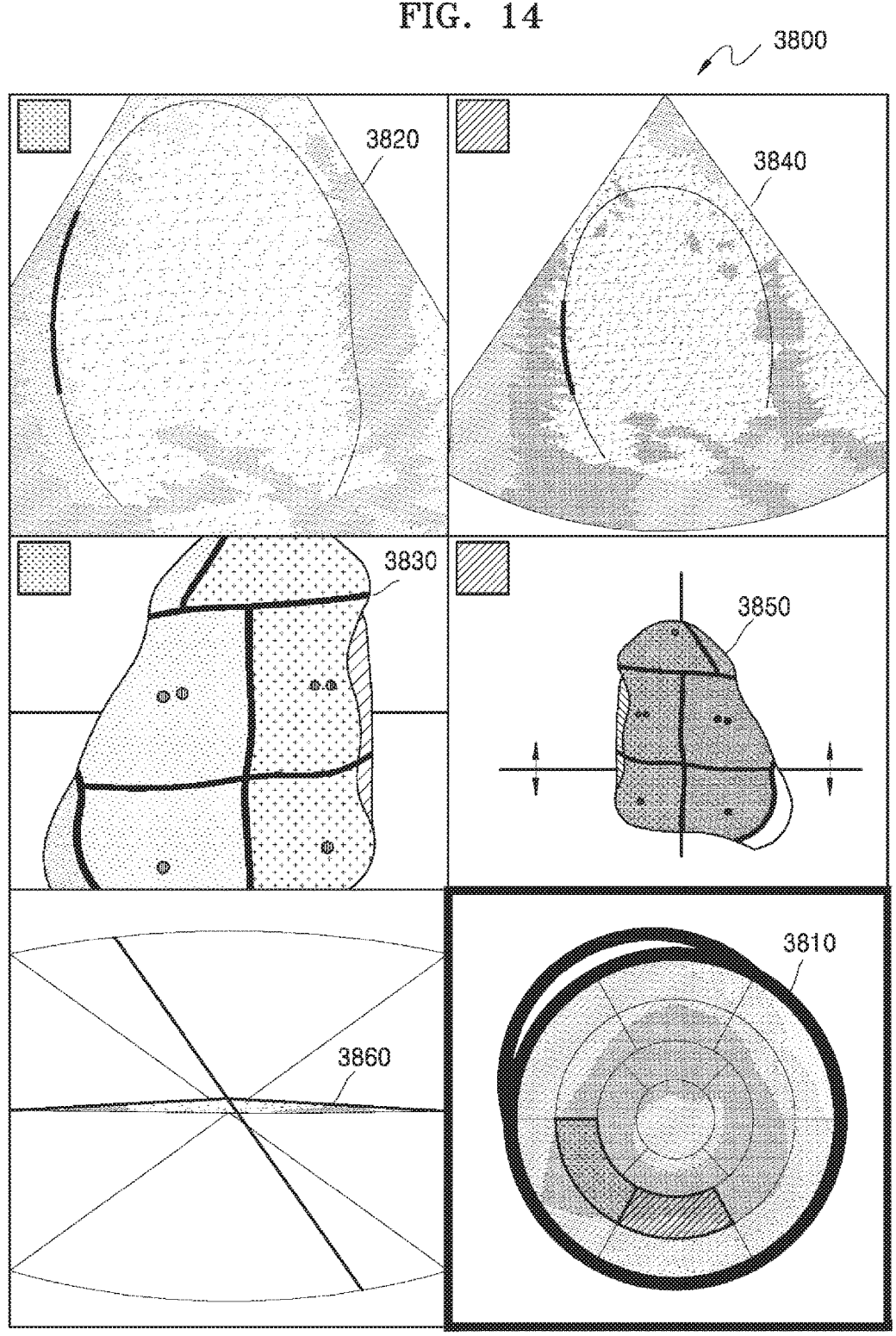
FIG. 14 is a diagram for explaining another example of an operation of a display apparatus according to an exemplary embodiment.

FIG. 14 is a diagram for explaining another example of an operation of the display apparatus 101 according to an exemplary embodiment.

FIG. 14 illustrates an example of a screen 3800 on which a model 3810 and images 3820, 3830, 3840, 3850, and 3860 are output.

As described above with reference to FIG. 13, the user may select at least one segment 3711 or 3712 from among the plurality of segments into which the model 3710 is partitioned. The image processor 1201 generates the 2D and 3D images 3720 and 3730 corresponding to the segment 3711 and the 2D and 3D images 3740 and 3750 corresponding to the segment 3712. The display 1401 displays the 2D and 3D images 3720, 3730, 3740, and 3750 on the screen 3700.

Subsequently, the user may enlarge or reduce at least one of the 2D and 3D images 3720, 3730, 3740, and 3750. For example, the user may enlarge or reduce at least one of the 2D and 3D images 3720, 3730, 3740, and 3750 by performing a gesture on the 2D and 3D images 3720, 3730, 3740, and 3750 or by using an input device.

For example, if a user input for enlarging the 2D image 3720 is received, the display 1401 displays an enlarged version 3820 of the 2D image 3720 on the screen 3800. Furthermore, since the 3D image 3730 shows the same ROI as the 2D image 3720, even when the user input for enlarging the 2D image 3720 is received, the display 1401 displays an enlarged version 3830 of the 3D image 3730 together with the enlarged version 3820.

Although FIG. 14 shows examples of the enlarged versions 3820 and 3830 of the 2D and 3D images 3720 and 3730 shown in FIG. 13, when a user input for reducing an image is received, a reduced version of the 2D or 3D image 3720 or 3730 may be displayed as described above with reference to FIG. 14.

Figure 15:
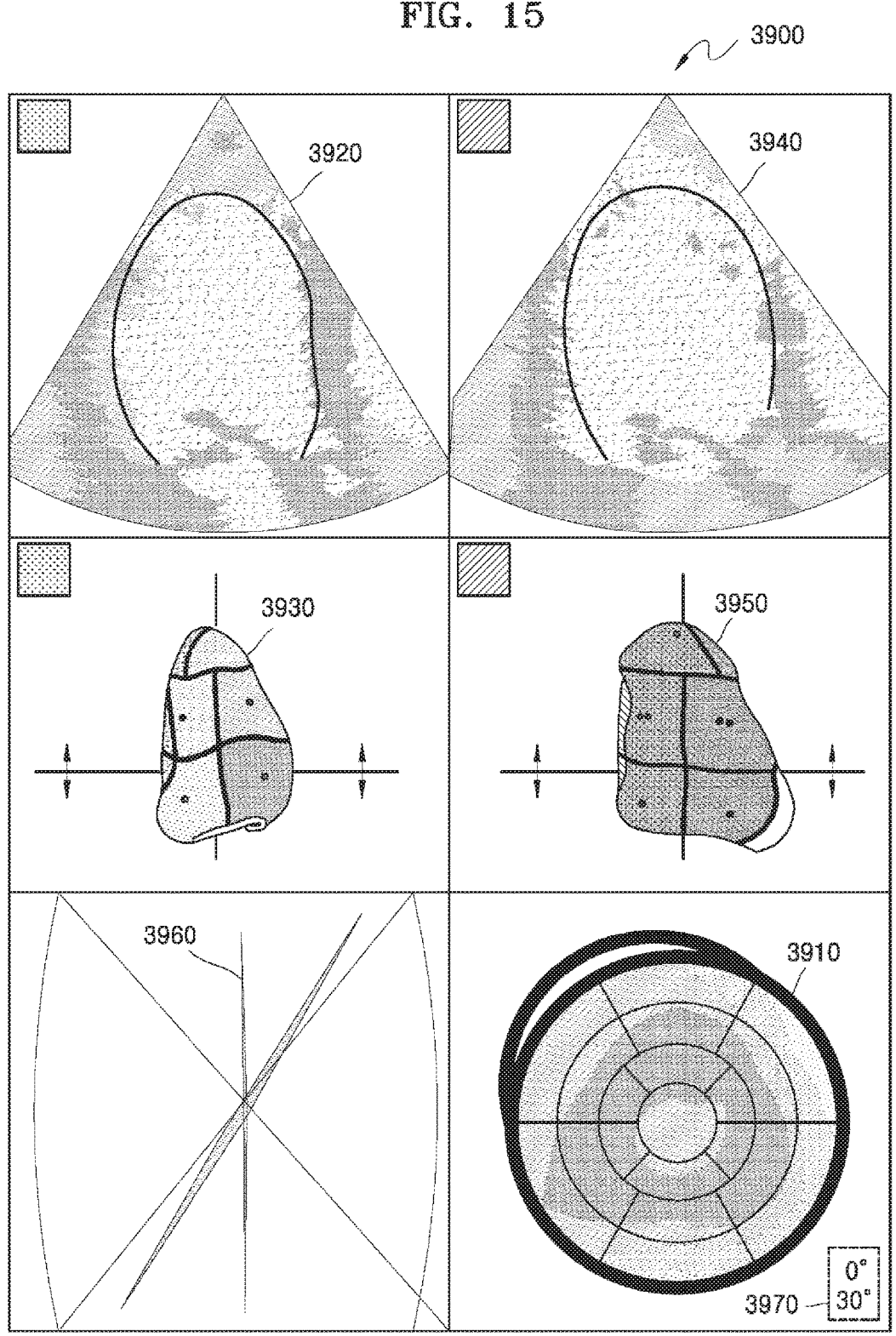
FIG. 15 is a diagram for explaining another example of an operation of a display apparatus according to an exemplary embodiment.

FIG. 15 is a diagram for explaining another example of an operation of the display apparatus 101 according to an exemplary embodiment.

FIG. 15 illustrates an example of a screen 3900 on which a model 3910 and images 3920, 3930, 3940, 3950, and 3960 are output.

As described above with reference to FIG. 7, the user may select an ROI in the model 3110 output on the initial screen 3100. In this case, a user input may be an input for designating an angle corresponding to the ROI. For example, the user may designate an angle corresponding to the ROI by using an input device. The angle corresponding to the ROI may be an angle with respect to a predetermined axis. For example, the predetermined axis may be determined in a vertical or horizontal direction of the model 3910, but is not limited thereto.

When a user input for designating an angle is received, the display 1401 displays the designated angle in a region 3970 of the screen 3900. The image processor 1201 uses a cross-section corresponding to the designated angle as an ROI to generate a 2D image 3920 and a 3D image 3930. The display 1401 then displays the generated 2D and 3D images 3920 and 3930 on the screen 3900.

Furthermore, the user may designate another angle as well as the previously designated angle. When a user input for designating the other angle is received, the display 1401 additionally displays the other designated angle in the region 3970 of the screen 3900. The image processor 1201 uses a cross-section corresponding to the other designated angle as an ROI to generate a 2D image 3940 and a 3D image 3950, which both show the ROI. The display 1401 may display the 2D image 3940 and the 3D image 3950 on the screen 3900.

Furthermore, the display 1401 may display an image 3960 showing a position relationship between the 2D images 3920 and 3940 on the screen 3900.

Figure 16:
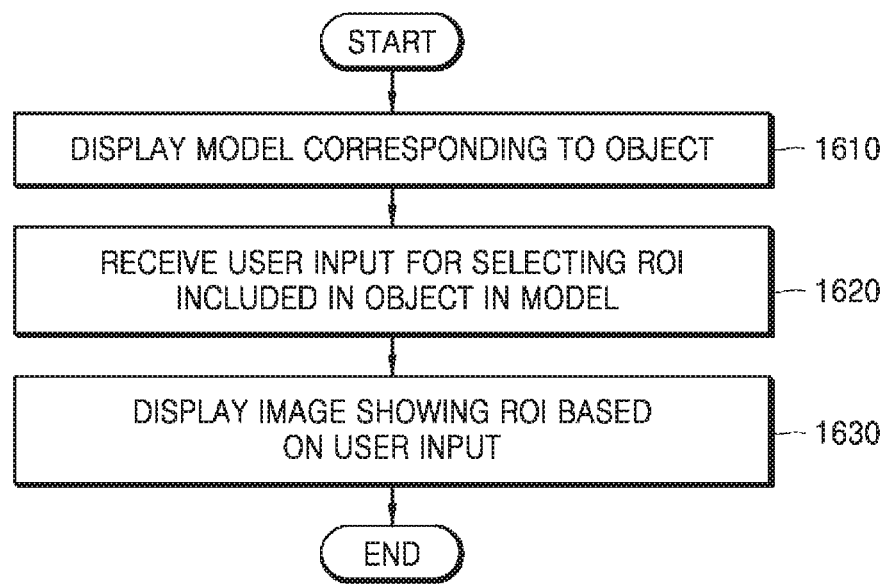
FIG. 16 is a flowchart of a method of displaying an image showing an object according to an exemplary embodiment.

FIG. 16 is a flowchart of a method of displaying an image showing an object according to an exemplary embodiment.

Referring to FIG. 16, the method of displaying an image showing an object includes operations sequentially processed by the ultrasound diagnosis systems 1000 and 1001 of FIGS. 1A and 1B and 1002 of FIG. 2 or the display apparatus 101 of FIG. 5. Thus, even when omitted hereinafter, the above descriptions with respect to the ultrasound diagnosis systems 1000 and 1001 of FIGS. 1A and 1B and 1002 of FIG. 2 or the display apparatus 101 of FIG. 5 may also apply to the method of FIG. 16.

A display displays a model corresponding to an object (operation 1610).

For example, an image processor may generate a model corresponding to an object, and the display may display the generated model on a screen. For example, the image processor may generate a model corresponding to an object currently being scanned and transmit the generated model to the display. As another example, the image processor may generate models for respective applications in advance, store the generated models in a memory, and read out a model for an application corresponding to the object from the memory. In this case, an application refers to a diagnostic field, and the type of application may be determined based on a part or internal organ of a human or animal body.

A model refers to an image showing an outlined shape of the object. In this case, the object may be an internal organ, and the model may be a 2D image showing an outlined shape of the internal organ.

An input unit receives a user input for selecting, from the model, an ROI of the object (operation 1620).

In this case, the ROI refers to a region of an object that a user desires to observe with focused attention. For example, the ROI may be a region corresponding to one cross-section of the object or a portion of a surface of the object.

For example, the user input may be a signal for selecting two different points in the model or a signal for changing a position of at least one of two different vectors represented in the model. Furthermore, the user input may be a signal for selecting one of a plurality of circles represented in the model or for drawing a circle on the model. Furthermore, the user input may be a signal for selecting a point in the model or for selecting one of a plurality of segments into which the model is partitioned. Furthermore, the user input may be a signal for enlarging or reducing a shape of the ROI included in the object or for designating an angle corresponding to the ROI.

The display displays an image showing the ROI based on the user input (operation 1630). In detail, the image processor generates an image showing the ROI based on the user input, and the display displays the image generated by the image processor. For example, the image processor may generate a cross-section of the object as a 2D and/or 3D image.

As described above, according to the exemplary embodiments, a model representing an object may be displayed on a screen, thereby allowing a user to easily identify the type of the object depicted in an image. Furthermore, by providing an operation that allows the user to select an ROI by using a model, the user may easily obtain an image showing the ROI.

The above method according to the exemplary embodiment can be recorded in programs that can be executed on a computer and be implemented through general purpose digital computers which can run the programs using a non-transitory computer-readable recording medium. Data structures described in the above method can also be recorded on a non-transitory computer-readable medium in a variety of ways, with examples of the medium including recording media, such as magnetic storage media (e.g., ROM, RAM, USB, floppy disks, hard disks, etc.) and optical recording media (e.g., CD-ROMs or DVDs).

While one or more embodiments have been described with reference to the figures, it will be understood by those of ordinary skill in the art that various changes in form and details may be made therein without departing from the spirit and scope of the inventive concept as defined by the following claims. Thus, it should be understood that the exemplary embodiments described therein should be considered in a descriptive sense only and not for purposes of limitation. The scope of the present inventive concept is defined not by the detailed description thereof but by the appended claims, and all differences within the scope of the appended claims and their equivalents will be construed as being included in the present inventive concept.

What is claimed is:

1. A method of displaying an image showing an object, the method comprising:
    displaying a model corresponding to the object;
    receiving a user input for selecting, from the model, a region of interest (ROI) included in the object; and
    displaying an image showing the ROI based on the user input,
    wherein the receiving of the user input comprises receiving a user input for selecting two different points in the model, generating a vector based on the received user input, identifying a cross-section of the object corresponding to the vector, and setting the cross-section of the object as the ROI,
    wherein the model is formed by projecting a 3D shape of the object onto a plane.

2. The method of claim 1, wherein the displaying of the image showing the ROI comprises displaying the image showing the ROI corresponding to a vector between the two different points.

3. The method of claim 1, wherein the displaying of the image showing the ROI comprises displaying the image showing the ROI corresponding to a normal vector, and
    wherein the normal vector comprises a normal vector that is orthogonal to a vector between the two different points.

4. The method of claim 3, further comprising receiving a user input for changing a position of at least one of the vector between the two different points and the normal vector,
    wherein the displaying of the image showing the ROI comprises displaying the image showing the ROI corresponding to the at least one of the vector and the normal vector whose position has been changed.

5. The method of claim 1, wherein the receiving of the user input comprises receiving a user input for selecting one of a plurality of circles depicted on the model, and
    wherein the displaying of the image showing the ROI comprises displaying the image showing the ROI corresponding to the selected circle.

6. The method of claim 1, wherein the receiving of the user input comprises receiving a user input for selecting a point in the model, and
    wherein the displaying of the image showing the ROI comprises displaying the image showing the ROI corresponding to a vector between the selected point and a central point of the model.

7. The method of claim 1, wherein the receiving of the user input comprises receiving a user input for selecting one of a plurality of segments into which the model is partitioned, and
    wherein the displaying of the image showing the ROI comprises displaying the image showing the ROI corresponding to the selected segment.

8. The method of claim 1, wherein the receiving of the user input comprises receiving a user input for designating an angle corresponding to the ROI.

9. The method of claim 1, further comprising:
    receiving a user input for requesting enlargement or reduction of a shape of the ROI in the displayed image; and
    displaying an image showing the ROI whose shape has been enlarged or reduced based on the user input.

10. The method of claim 1, wherein the object comprises an internal organ, and the model comprises a two-dimensional (2D) image showing the internal organ.

11. The method of claim 1, wherein the image showing the ROI comprises a 2D image or a three-dimensional (3D) image.

12. A non-transitory computer-readable medium having recorded thereon a program for executing the method of claim 1 on a computer.

13. An apparatus for displaying an image showing an object, the apparatus comprising:
    a display configured to display a model corresponding to the object;
    an input interface configured to receive a user input for selecting, from the model, a region of interest (ROI) included in the object; and
    an image processor configured to generate an image showing the ROI based on the user input,
    wherein the display displays the generated image,
    wherein the input interface receives a user input for selecting two different points in the model, and
    wherein the image processor generates a vector based on the received the user input, identifies a cross-section of the object corresponding to the vector, and sets the cross-section of the object as the ROI,
    wherein the model is formed by projecting a 3D shape of the object onto a plane.

14. The apparatus of claim 13, wherein the image processor generates the image showing the ROI corresponding to a vector between the two different points.

15. The apparatus of claim 13, wherein the image processor generates the image showing the ROI corresponding to a normal vector, and
    wherein the normal vector comprises a normal vector that is orthogonal to a vector between the two different points.

16. The apparatus of claim 15, wherein the input interface receives a user input for changing a position of at least one of the vector between the two different points and the normal vector, and wherein the image processor generates the image showing the ROI corresponding to the at least one of the vector and the normal vector whose position has been changed.

17. The apparatus of claim 13, wherein the input interface receives a user input for selecting one of a plurality of circles depicted on the model, and wherein the image processor generates the image showing the ROI corresponding to the selected circle.

18. The apparatus of claim 13, wherein the input interface receives a user input for selecting a point in the model, and wherein the image processor generates the image showing the ROI corresponding to a vector between the selected point and a central point of the model.

19. The apparatus of claim 13, wherein the input interface receives a user input for selecting one of a plurality of segments into which the model is partitioned, and wherein the image processor generates the image showing the ROI corresponding to the selected segment.

20. The apparatus of claim 13, wherein the input interface receives a user input for designating an angle corresponding to the ROI.

21. The apparatus claim 13, wherein the input interface receives a user input for requesting enlargement or reduction of a shape of the ROI in the displayed image, and wherein the image processor generates an image showing the ROI whose shape has been enlarged or reduced based on the user input.

22. The apparatus of claim 13, wherein the object comprises an internal organ, and the model comprises a two-dimensional (2D) image showing the internal organ.

23. The apparatus of claim 13, wherein the image showing the ROI comprises a 2D image or a three-dimensional (3D) image.

\* \* \* \* \*